United States Patent
Johnson

(10) Patent No.: US 8,029,411 B2
(45) Date of Patent: Oct. 4, 2011

(54) SYSTEMS AND METHODS OF MONITORING EXERCISES AND RANGES OF MOTION

(75) Inventor: Paul R. Johnson, Waukesha, WI (US)

(73) Assignee: Honeywell International Inc., Morristown, NJ (US)

( * ) Notice: Subject to any disclaimer, the term of this patent is extended or adjusted under 35 U.S.C. 154(b) by 578 days.

(21) Appl. No.: 11/831,590

(22) Filed: Jul. 31, 2007

(65) Prior Publication Data

US 2009/0033770 A1 Feb. 5, 2009

(51) Int. Cl.
*A63B 71/00* (2006.01)
(52) U.S. Cl. .............................. 482/9; 482/902; 434/257
(58) Field of Classification Search .............. 482/9, 902; 434/257
See application file for complete search history.

(56) References Cited

U.S. PATENT DOCUMENTS

| 5,486,001 | A | * | 1/1996 | Baker | 473/266 |
| 5,826,578 | A | * | 10/1998 | Curchod | 600/595 |
| 6,126,449 | A | * | 10/2000 | Burns | 434/252 |
| 6,293,802 | B1 | * | 9/2001 | Ahlgren | 434/252 |
| 7,264,554 | B2 | * | 9/2007 | Bentley | 473/222 |
| 7,658,695 | B1 | * | 2/2010 | Amsbury et al. | 482/8 |
| 2005/0285941 | A1 | | 12/2005 | Haigh | |
| 2006/0293613 | A1 | | 12/2006 | Fatehi | |
| 2007/0026958 | A1 | * | 2/2007 | Barasch et al. | 473/266 |

* cited by examiner

*Primary Examiner* — David Ometz
*Assistant Examiner* — Dillon Durnford Geszvain
(74) *Attorney, Agent, or Firm* — Husch Blackwell

(57) ABSTRACT

Systems and methods are provided for remotely a monitoring an individual's ability to carry out a various exercise activities and to evaluate the individual's range of motion. The individual can stand or sit in the field of view of the camera and carry out a set of base line activities. The baseline activities can be stored for subsequent retrieval and analysis. Based on the results of that evaluation, other activities can be prescribed for the individual to systematically carry out. The results of the subsequent activities can be evaluated and compared to the result of the base line activities to determine how the activities should be revised or whether other treatments are required or appropriate.

15 Claims, 4 Drawing Sheets

SYSTEMS AND METHODS OF MONITORING EXERCISES AND RANGES OF MOTION

FIELD

The invention pertains to monitoring patient abilities to carry out exercises which exhibit various ranges of motion. More particularly, the invention pertains to such systems and methods which provide for remote review and monitoring of such patient activities.

BACKGROUND

Individuals that have range of motion limitations due to either disease or surgical procedures often need to be monitored. One way that such monitoring can be carried out is to have the patient physically meet with a physician or a therapist for an evaluation. While useful, and the historical norm, physically consulting with a physician or therapist is often very difficult for a debilitated or ill individual. Additionally, it may be difficult for the individual to obtain a short term appointment due to both the physician and therapist being very busy.

There is an ongoing need to be able to monitor individuals, for example, for range of motion, in a way that is not only cost effective but which provides relatively short-term access by the individual to the respective medical professional. It would thus be desirable to be able to provide information pertaining to exercise ability and/or range of motion to an individual's physician or therapist on a short-term basis without necessarily requiring that the individual physically meet with his or her physician or a therapist. Being able to conduct remote evaluations of the individual's range of motion and/or exercise abilities can be especially advantageous relative to those individuals who are not able to travel easily to either the doctor's office or the therapist's office for an appointment.

DETAILED DESCRIPTION

Figure 1:
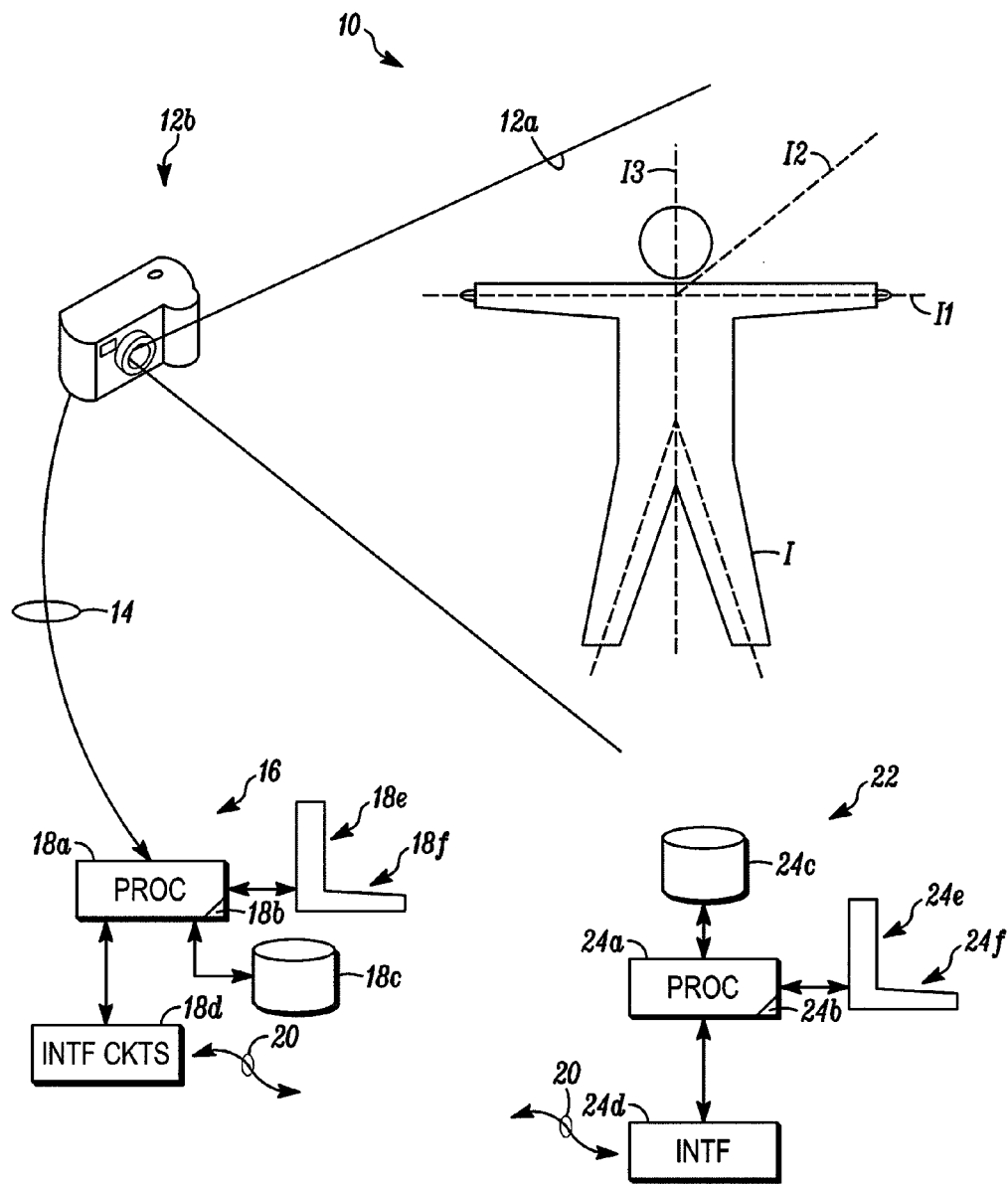
FIG. 1 is an overall view of the system in accordance with the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In one embodiment of the invention, a video capture device (camera, video camera, etc) could be utilized to establish the mobility of patients that have restricted movement due to illnesses or recent surgical procedures and have a physical therapy element to their rehabilitation. The patient would first stand in front of the camera and do a set of basic movements, or activities, in order to establish a base line for the movements that he/she can already do. For instance, raising their arms to a horizontal and then raising them as high as they can go comfortably. Information pertaining to the baseline activities could then be stored locally, or transmitted to a displaced monitoring system.

The camera could send back data to a local or displaced monitor that would calculate the person's center lines of the body and extremities. Once that has been established, the angle of the arm from the base line (arms straight out) could then be measured. The patient would then carry out this "exercise," or activity as requested by the physician. The data than could be compared to the previous data in order to assess the success or failure of the individual's rehabilitation.

In yet another embodiment, the camera could be combined with a display unit to prescribe additional activities or movements for the individual to carry out. The results could also be stored locally or transmitted to the displaced monitoring system.

In another aspect of the invention, the individual or patient, in the field of view of the camera would be able to view a video screen and reach toward, or "touch" a shape, in space, displayed on the screen. The ability of that person to move toward and/or successfully "contact" the displayed shape could be stored in the local data base for later review and analysis. A sequence of shapes displayed at different locations on the display can be presented for response by the individual. The exercises or activities can present varying degrees of difficulty to the individual. Results of the individual's responses to the sequence can be stored and forwarded to a physician or therapist for review and to provide input as to the next sequence to forward for the individual to respond to.

FIG. 1 illustrates a system 10 which can interact with an individual I located within a field of view 12*a* of a camera 12*b*. Camera 12*b* produces a digital output of an image in the field of view 12*a* and transmits same via wired or wireless medium 14 to a local unit, indicated generally at 16 of the system 10. The local unit 16 includes a programmable processor 18*a* which is in communication with the camera 12*b* via the medium 14. Associated with processor 18*a* is executable control software 18*b* as described in more detail subsequently.

The local unit 16 also includes a mass storage unit 18*c* which could be magnetic or optical, coupled to the processor 18*a*. The unit 18*c* can store, under the control of the processor 18*a* and software 18*b*, images from the camera 12*b*. Local unit 16 can communicate via interface circuits 18*d* and a wired or wireless medium 20 with a displaced monitoring unit indicated generally at 22.

The local unit 16 can also include a local display device indicated generally at 18*e* and associated manual input device indicated generally at 18*f* which could include a keyboard, track ball or the like all without limitation. The communication devices 18*e*, 18*f* in combination with the processor 18*a* and software 18*b* can implement a graphical user's interface for communication with the individual I.

It will be understood that the display device 18*e* could be coupled to the input device 18*f* or separate therefrom all without departing from the spirit and scope of the invention. Alternately, the display device 18*e* could be duplicated by yet another display unit, for example a wall mountable unit, located for viewing by the individual I.

The remote monitoring unit 22 can include a programmable processor as indicated generally at 24*a*, associated executable software 24*b*, a storage unit 24*c*, magnetic or optical, whereat information in connection with the activities of the individual I can be stored and reviewed. Unit 22 can also include interface circuitry 24*d* for receiving information from and coupling information to the unit 16, via the medium 20. The unit 22 can also include a display device 24*e* and a manual input device such as a keyboard, trackball, mouse and the like all without limitation 24f. As will be understood by those of skill in the art, the processor 24a, and software 24b can implement a graphical user's on the display unit 24e.

System 10 can be used to obtain a base line of mobility of the individual I. For example, if the mobility of the individual I has been restricted due to illness or one or more surgical procedures, it would be desirable to be able to remotely monitor, via the unit 22, progress of the individual I through one or more therapies. In this regard, base line information can be established by requesting that the individual I step into the field of view 12a of the camera 12b and carry out a set of basic movements, as requested either verbally or visually via the local unit 16, or a therapist or physician either locally or via telephone.

The individual I could be requested to raise his or her arms to horizontal position as indicated generally at 11 in FIG. 1. This position information could be coupled via the camera 12b to the local unit 16. The individual I could then be requested to raise his or her arms as they can as far as possible or comfortably. This position indicated generally at 12 in FIG. 1 could then be coupled via camera 12b to the local unit 16. The center lines for the individual I indicated generally at 12, 13 can be established. The angle of displacement between the horizontal position 11 and displaced upward position 12 can be established by local unit 16, and stored in data base 18c for subsequent use.

Base line information can be coupled via interface circuitry 18d and medium 20 to displaced monitoring unit 22 for evaluation by a physician or therapist. Those individuals can consider the images and information perceived from the camera 12b and establish a therapy program, which might include a series of activities for the individual I. That program can be transmitted to the local unit 16 to be carried out by the individual I. In this regard, the therapy program could include a sequence of activities which would involve the individual I moving himself/herself in the field of view 12a in accordance therewith. Information as to the ability of the individual I to carry out the activity sequence can then be coupled via camera 12b and local unit 16 to the remote monitoring unit 22 for follow-up and further evaluation.

Figure 2:
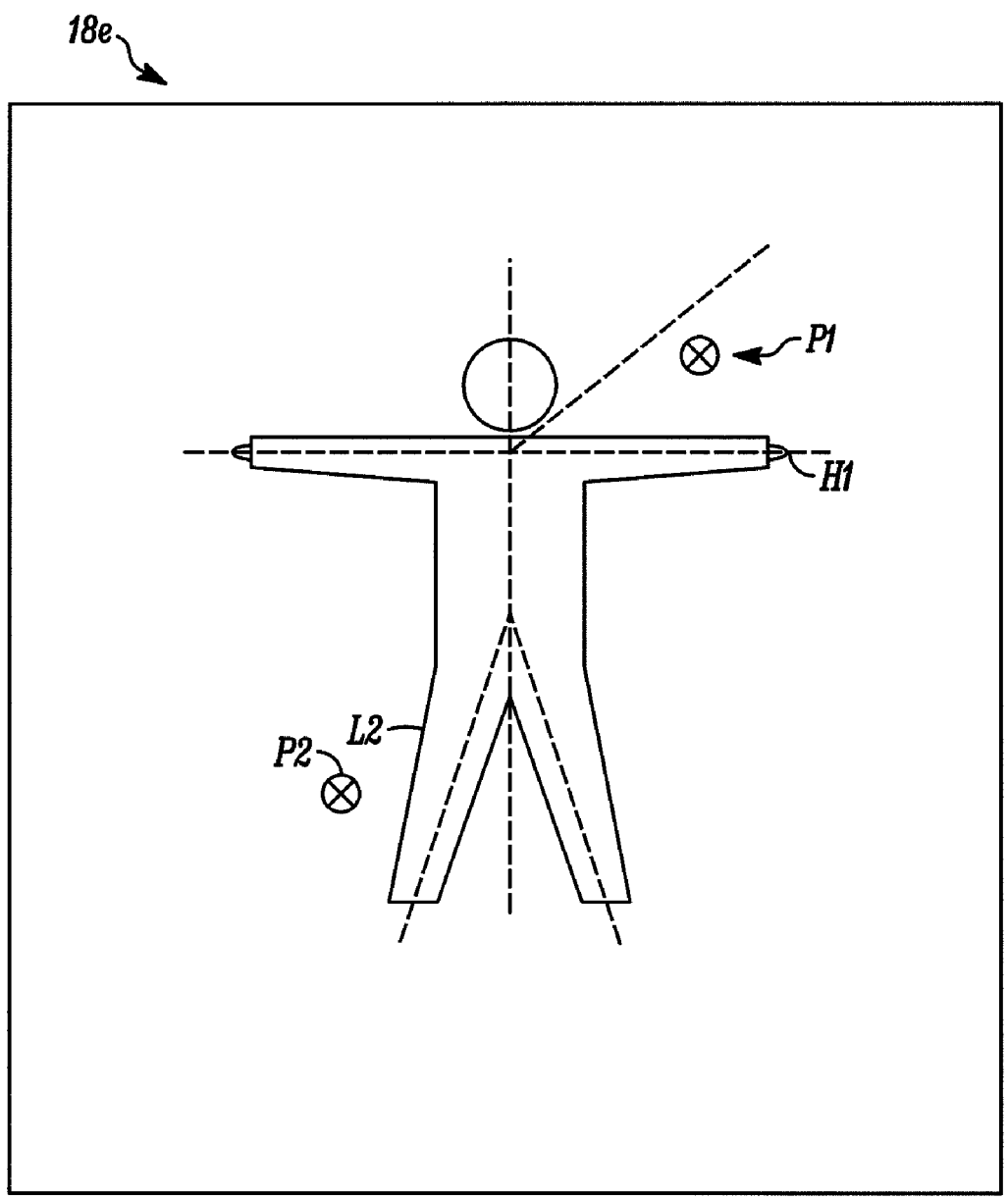
FIG. 2 is an exemplary image of an activity to be carried out by an individual interacting with the system of FIG. 1.

FIG. 2 illustrates an image presentable on the display unit 18e to the individual I which presents a representation of the individual I as well as first and second exemplary activities to be carried out by the individual I. For example and without limitation a first activity could be to request the individual I move his or her hand H1 to indicated position P1 on the display unit 18e as illustrated in FIG. 2. Once the individual has moved his or her hand H1 as close as possible to the position P1, the individual can audibly indicate to the unit 16 that he or she has completed that activity. Subsequently, a second position P2 can be presented on the display as in FIG. 2 indicative of a position to which the individual I is to move his or her leg L2. Once again, the individual I can indicate his or her completion of the activity verbally to the system 16.

As those with skill in the art will understand, the individual I receives immediate real time feedback via the display device 18e as to his or her progress in obtaining the desired objective of the activity, namely, positioning hand H1 at location P1 or leg H2 at position P2. Also, information can be accumulated at storage unit 18c and transmitted to remote unit 22 for consideration and evaluation.

Figure 3:
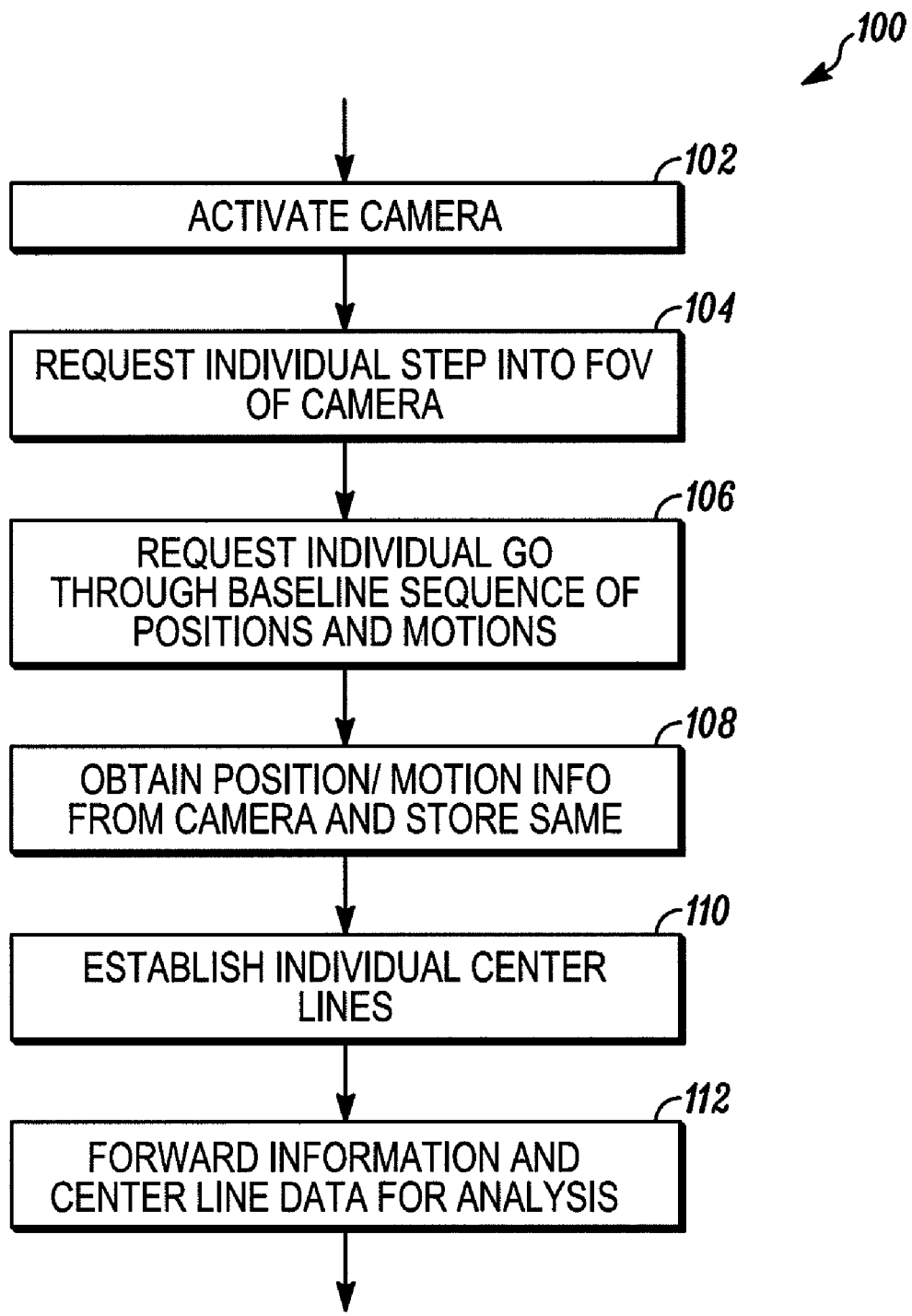
FIG. 3 is a flow diagram illustrating some aspects of a method which embodies the invention.

Aspects of method 100 are illustrated in a flow diagram in FIG. 3. Initially a camera such as the camera 12 is activated at 102. A request is then made for an individual to step into the field of view of the camera as at 104. A request is then made for the individual to go through a base line sequence of positions and motions as at 106.

Positions and motion information is obtained from the camera such as the camera 12b and stored, for example in unit 18c as at 108. Using the acquired information, individual center lines can then be established as at 110. The information and center line results can then be forwarded to a displaced monitoring system as at 112.

Figure 4:
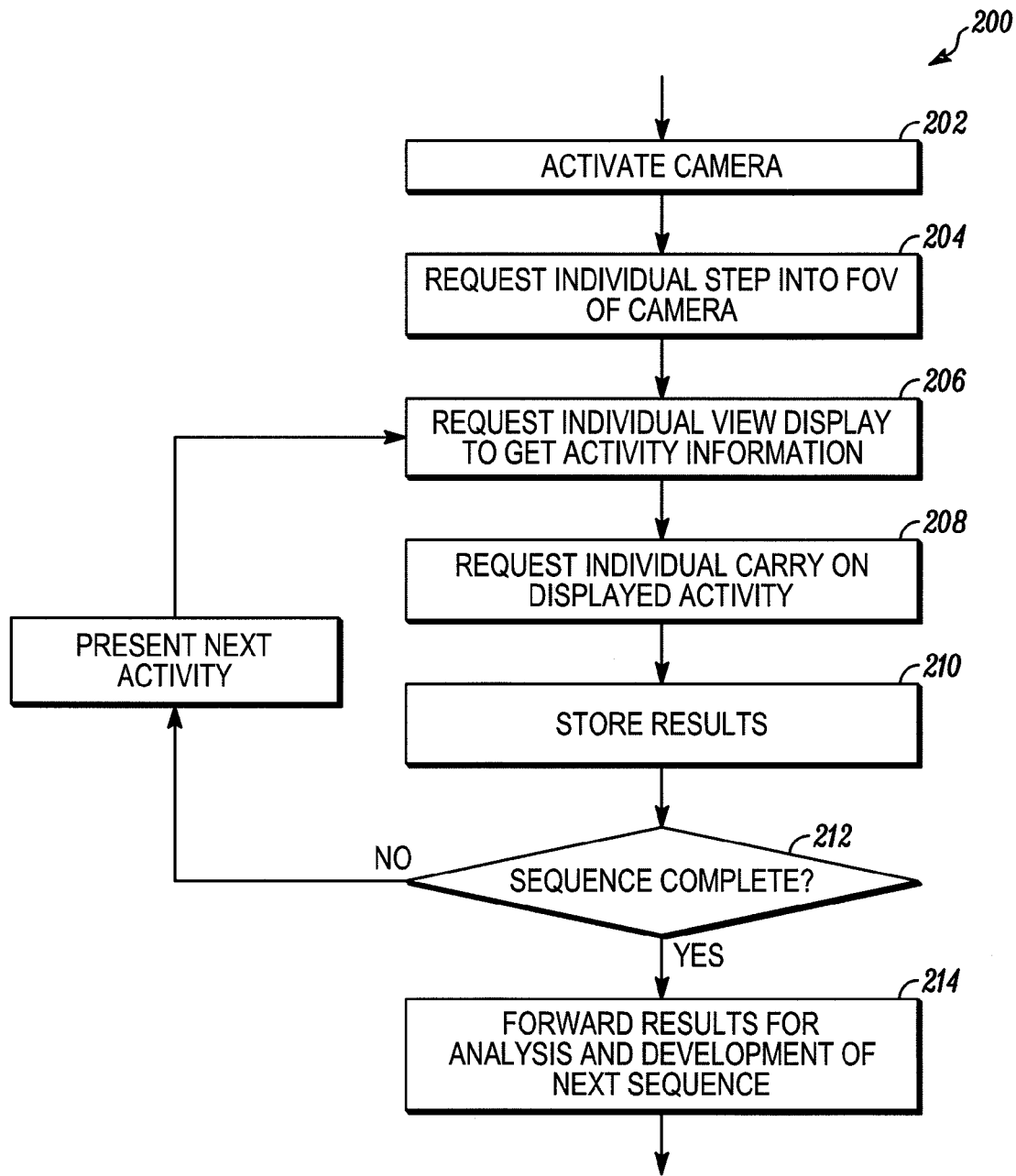
FIG. 4 is a flow diagram which illustrates additional aspects of the method of FIG. 3.

Subsequent to obtaining base line information, as in FIG. 3, a sequence of activities can be presented to the individual I in accordance with method 200 of FIG. 4. A camera such as 12b can be activated as at 202.

A request can then be made at the individual I step into the field of view of the camera as at 204. The individual can then be requested to view a display, as in FIG. 2, to get activity information as in 206.

A request can then be made that the individual carryout the displayed activity as in 208. Results of the individual's carrying out the requested activity and be stored as at 210l.

If the activity sequence has been completed, as at 212, the information and results can be forwarded for analysis and development of the next sequence to an appropriate medical professional as at 214. In the alternative, if the sequence has not been completed the next activity can be presented to the individual I and as in 206, the individual can be requested to view the display as the display device 18e to get information as to the next activity to be carried out.

Those of skill will understand that variations in the above system in and processing associated therewith come within the spirit and scope of the present invention. For example, display 18e can be provided with a touch sensitive screen. In response to an activity display presented thereon, as in FIG. 2, the individual I can be requested to touch an appropriate portion of the display unit 18e for example the position P1 or the position P2. It will also be understood that the local unit 16 can be provided with voice output software and voice recognition software such that the individual I can communicate verbally therewith.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. An apparatus comprising:
a camera having a predetermined field of view;
control circuits coupled to the camera;
a device coupled to the control circuits that stores information from the camera; and
a multi-dimensional display device, coupled to the control circuits, the device projects an image of an individual onto the display device with the control circuits providing direction to the individual including indicators of a sequence of requested positions that evaluate a range of motion of the individual in the field of view adjacent the image of the individual, the control circuits receiving verbal indication from the individual upon completion of each requested position of the sequence of positions, said control circuits providing immediate feedback of the individual's progress in obtaining said requested position in response to said received verbal indication before presenting another position of the plurality of positions.

2. An apparatus as in claim 1 where information concerning the individual's response to the requested position is stored in the device by the control circuits.

3. An apparatus as in claim 2 which includes interface circuitry, coupled to the control circuits, that transmits information stored in the device to a displaced monitoring location.

4. An apparatus as in claim 3 which includes a monitoring station, at the displaced location, the monitoring station receives the information from the interface circuitry and includes a device for displaying representations of such information.

5. An apparatus as in claim 1 where the control circuits include a programmable processor and executable software which provide a set of baseline activities for the individual to emulate.

6. An apparatus as in claim 5 which includes software to evaluate information from the camera pertaining to the individual's response to the set of baseline activities.

7. An apparatus as in claim 6 which includes software that establishes a baseline profile for the individual and stores that profile at the device.

8. An apparatus as in claim 7 where information indicative of the individual's emulation of the target image is compared to the pre-stored baseline profile for that individual.

9. An apparatus as in claim 8 where, responsive to results of the comparison, the processor and software modify the target image.

10. An apparatus as in claim 9 which includes circuitry to emit verbal feedback to the user relative to the activities.

11. A method comprising:
control circuits providing a plurality of indicators of baseline activities that evaluate a range of motion of a user on a display for the user;
control circuits requesting that the user emulate the provided activities and receiving verbal feedback from the user that each activity has been completed;
a camera obtaining real-time images of the user as the user emulates the activities the real time images showing the indicators adjacent the user on the display; and
control circuits evaluating performance of the user from the real-time images.

12. A method as in claim 11 which includes visually providing target activities for the user.

13. A method as in claim 12 which includes at least one of verbally, or visually requesting that the user emulate the target activities.

14. A method as in claim 13 which includes evaluating the user's emulation of the target activities.

15. A method as in claim 14 which includes transmitting information relative to the user's emulation of the target activities to a displaced site for evaluation.

* * * * *